United States Patent [19]

Pietsch et al.

[11] Patent Number: 4,588,583

[45] Date of Patent: May 13, 1986

[54] SURGICAL MATERIAL

[75] Inventors: Hanns Pietsch, Hamburg; Volker Hohmann, Norderstedt; Detlef Kluck, Buxtehude, all of Fed. Rep. of Germany

[73] Assignee: Beiersdorf Aktiengesellschaft, Hamburg, Fed. Rep. of Germany

[21] Appl. No.: 545,035

[22] Filed: Oct. 25, 1983

[30] Foreign Application Priority Data

Dec. 11, 1982 [DE] Fed. Rep. of Germany ....... 3245956

[51] Int. Cl.$^4$ .................. A61K 6/08; A61K 31/78; C08K 5/10; C08F 265/06
[52] U.S. Cl. ...................... 424/81; 523/116; 524/110; 524/239; 524/247; 524/257; 524/310; 524/313; 524/317; 524/377; 524/533
[58] Field of Search ............. 523/116, 117; 524/310, 524/312, 533, 313, 317, 110, 247, 239, 257; 424/81

[56] References Cited

U.S. PATENT DOCUMENTS

| | | | |
|---|---|---|---|
| 1,980,483 | 11/1934 | Hill | 524/310 |
| 2,120,006 | 6/1938 | Strain | 524/310 |
| 2,377,041 | 5/1945 | Rogover | 524/310 |
| 2,439,374 | 3/1948 | Leader | 524/469 |
| 2,496,387 | 2/1950 | Fink | 524/310 |
| 2,599,400 | 6/1952 | Leerburger | 524/533 |
| 2,872,429 | 2/1959 | Schwartz | 524/310 |
| 3,789,029 | 1/1974 | Hodosh | 521/149 |
| 4,120,730 | 10/1978 | Trojer | 106/39.6 |
| 4,141,864 | 2/1979 | Rijke | 521/63 |
| 4,171,544 | 10/1979 | Hench | 3/1.9 |
| 4,282,140 | 8/1981 | Bousquet | 524/533 |
| 4,341,691 | 7/1982 | Anuta | 523/116 |
| 4,369,262 | 1/1983 | Walkowiak | 524/533 |
| 4,373,217 | 2/1983 | Draenert | 523/116 |
| 4,394,465 | 7/1983 | Podzun | 523/116 |
| 4,490,497 | 12/1984 | Evrard | 424/81 |

Primary Examiner—C. Warren Ivy
Attorney, Agent, or Firm—Sprung, Horn, Kramer & Woods

[57] ABSTRACT

Surgical material based on liquid monomeric and pulverulent polymeric acrylates and/or methacrylates, catalysts, accelerators and, if appropriate, customary additives, which passes via a plastic state into the solid state by mixing of the liquid and pulverulent components, and which contains 1–15% by weight, based on the total weight, of one or more non-toxic, liquid aliphatic, saturated mono-, di- or tri-carboxylic acids with 1–6 carbon atoms and, if appropriate, 1 or 2 hydroxyl groups, completely or partially esterified with mono-, di- or tri-hydric alcohols with 1–4 carbon atoms, or liquid ethylene glycols or 1,2- or 1,3-propylene glycols with in each case 2 to about 30 glycol units, these liquids having a boiling point above 100° C., preferably above 150° C.

15 Claims, No Drawings

SURGICAL MATERIAL

The invention relates to a surgical material based on liquid monomeric and pulverulent polymeric acrylates and/or methacrylates which passes via a plastic state into the solid state by the addition of catalysts and accelerators and, if appropriate, customary additives after the liquid and pulverulent components have been mixed. The compositions are suitable as so-called "bone cements", in particular for implanting artificial hip and knee joints or the like in the bone.

Bone cements based on methyl methacrylate/polymethyl methacrylate have been used in bone surgery for many years. They consist of a liquid component and a solid component which are stored separately and mixed before use. The mixture is pasty to cream-like and is used in this form, and hardening takes place in the body after use. The solid component usually consists of polymethyl methacrylate powder, the polymerization initiator and, if appropriate, an X-ray contrast agent, such as, for example, barium sulfate or zirconium dioxide. The powder can furthermore contain antibiotics, such as gentamycin, chopped fibers for reinforcing, such as carbon fibers, or bone growth-promoting additives, such as calcium phosphate. The liquid component consists of monomeric methyl methacrylate, an accelerator and, if appropriate, a dyestuff. The two components are mixed in a ratio of about 2:1 shortly before processing, can then be processed for about 4–6 minutes and have hardened in 6–15 minutes.

The advantages of such bone cements are their good compatibility with tissue material, the rapid hardening and the high strength of the hardened cement. However, these advantages are counteracted by the disadvantages of the relatively high temperatures which occur during polymerization and can lead to damage of the surrounding tissue and thereby to a loosening of the connection.

A further disadvantage of the "cements" based on methyl methacrylate which have hitherto been used for joint operations is the release of residual monomers. Monomeric methyl methacrylate enters the blood stream and can lead to fat embolisms, which can result in cardiocirculatory complications as serious as cardiac arrest.

These disadvantages are avoided by a bone cement according to German Pat. No. 2,552,070, which contains, as the liquid component, an emulsion of methyl methacrylate, water, emulsifier and accelerator. Bone cements which are prepared by this process have a lower maximum hardening temperature, a lower content of residual monomers and an improved wetting of the unevenness of the bone.

Besides these advantages in application, however, the use of emulsions also has disadvantages, chiefly in their handling. The emulsions are viscous liquids of 200–800 MPa.s, which can only be emptied out of the ampoules by shaking several times. This shaking means a troublesome, time-consuming action during the operation, and meticulous care must be taken that the ampoule is emptied completely and no drops fall beside the site when the emulsion is beaten out. In addition, an aqueous emulsion is sensitive to frost during storage.

The object of the invention was therefore to develop a surgical material which, although it also has the advantages described in German Pat. No. 2,552,070, does not have the disadvantages mentioned.

Surprisingly, it has been found that surgical compositions with a reduced evolution of heat, a reduced content of residual monomers, very good wetting properties and, moreover, improved adhesion towards implant alloys are obtained by a process wherein no aqueous emulsion is used as the liquid component, but 1–15% by weight, based on the total weight, of one or more non-toxic, non-polymerizable organic liquids which are miscible with methyl methacrylate and have a boiling point above 100° C., preferably above 150° C., and, if appropriate, surface-active substances, are added to the composition.

These organic liquids, which do not participate in the polymerization reaction because they contain no ethylenically unsaturated double bonds, are liquid esters, that is to say aliphatic, saturated mono-, di- or tri-carboxylic acids with 1–6 carbon atoms and, if appropriate, 1 or 2 hydroxyl groups, completely or partially esterified with mono-, di- or tri-hydric alcohols with 1–4 carbon atoms, or are liquid ethers, that is to say ethylene glycols or 1,2- or 1,3-propylene glycols with in each case 2 to about 30 glycol units. In polymer chemistry, such liquids are also called plasticizers. It is surprising that, in the proportions indicated, no "plasticizing" takes place and the resulting hardened compositions have the same hardness as polymethyl methacrylate which does not contain these liquids.

Suitable liquid esters are, in particular: glycol mono- and di-formate, -acetate, -propionate, -glycolate and -lactate, glycerol mono-, di- and tri-formate, -acetate, -propionate, -glycolate and -lactate, methyl, ethyl, propyl and butyl glycolate, methyl, ethyl, propyl and butyl lactate, monomethyl and dimethyl malate, monoethyl and diethyl malate, monopropyl and dipropyl malate, monobutyl and dibutyl malate, monoethyl and dimethyl tartrate, monoethyl and diethyl tartrate, monopropyl and dipropyl tartrate, monobutyl and dibutyl tartrate, mono-, di- and tri-methyl citrate, mono-, di- and tri-ethyl citrate, mono-, di- and tri-propyl citrate and mono-, di- and tri-butyl citrate.

The esters and ethers mentioned, of which glycerol triacetate (triacetin), triethyl citrate and liquid polyethylene glycols, polypropylene 1,2-glycols and polypropylene 1,3-glycols with a degree of polymerization of n=5–15 are particularly preferred, have the common property that they contain non-polar and polar groups in a ratio of 1:1 to 3:1, non-polar groups being understood as —CH₃, —CH₂—,

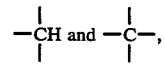

and polar groups being understood as —OH, —O— and —COOR. This circumstance seems decisive for the fact that the substances are miscible with monomeric methyl methacrylate, which is the liquid component of the bone cement, in all proportions and form a clear solution, and that at least the esters are also a good solvent for the polymethyl methacrylate. The ethers are a swelling agent for the polymer.

A further property of the liquids mentioned is their very good biological tolerance, which means a number of them can also be used as solvents or solubilizing agents in pharmaceutical formulations.

In the surgical material according to the invention, the liquids have, inter alia, the function of giving the plastic composition a creamy consistency during the pasting phase and of reducing the viscosity. It has been found that they form two groups in respect of the properties of the bone cements prepared using them: 1. The group of ethers, that is to say ethylene glycols and propylene glycols, and of esters of glycol and glycerol with carboxylic acids containing no hydroxyl groups give bone cements which are comparable to those of German Pat. No. 2,552,070. 2. The group of esters of hydroxycarboxylic acids, such as glycollic acid, lactic acid, malic acid, tartaric acid or citric acid, give bone cements which clearly differ from those of the first group in that the mixtures containing these compounds have a marked tackiness in the plastic state.

The liquid mixtures of methyl methacrylate, the liquid described, accelerator and, if appropriate, 0-5% of a surface-active agent are stirred with a powder mixture before use. This powder mixture consists of polymethyl methacrylate bead polymer, polymerization initiator and, if appropriate, an X-ray contrast agent. The present invention does not relate to this powder mixture. The ratio of powder to liquid phase is 1-3, preferably 1.5-2.5. The mass formed after mixing the powder and liquid component contains from 1 to 15% of the organic liquid according to the invention, which is contained in the liquid component.

Plastic bone cement mixtures become usually free from tackiness some time after the liquid and pulverulent components have been brought together. They can then be taken in the hand and shaped without residues remaining on the hand or glove.

The time from mixing of the two components to freedom from tackiness is called the "pasting time" according to DIN-ISO 5833. Bone cements according to the invention containing compounds of the first group mentioned reach this tack-free state before introduction into the bone. Bone cements according to the invention containing compounds of the second group do not reach this state of freedom from tackiness before hardening. They can preferably be applied with a so-called bone cement syringe and have excellent adhesion to polar materials, such as metallic prostheses, and bone.

As already described, the liquid ethers and esters are preferably used together with monomeric methyl methacrylate and the accelerator in a mixture as the "liquid component". However, it is also possible to stir these compounds separately, for example as a further component, with the powder. The nature of the addition is not critical for the properties of the hardened bone cement. However, the processing properties can thereby be influenced.

In the preferred embodiment of the surgical material, in which the ethers and esters are admixed to the liquid monomer, the liquid phase essentially consists of 94.5-62% by weight of monomeric methyl methacrylate, if appropriate with a low content of other modified acrylate derivatives, 5-30% by weight, preferably 15-20% by weight, of the liquid esters and/or ethers mentioned, 0.5-3% by weight of accelerator and 0-5% by weight of surface-active substances.

For better storage stability, the methyl methacrylate is thereby stabilized with 50-100 ppm of hydroquinone or hydroquinone monomethyl ester.

N,N-Dimethyl-p-toluidine, N,N-dimethylaniline, N,N-dimethylxylidines or N,N-dimethyl-anisidines or their N-monomethyl derivatives, preferably the first compound, are usually employed as accelerators for the subsequent polymerization reaction.

It has been found that such mixtures give good wetting of the uneven bone surface; this and the ability to fill even the finest grooves can, however, be improved still further by adding a certain amount of surface-active (interface-active) substances. Compounds which are preferably suitable for this are non-ionic and cationic compounds, such as, for example, fatty acid esters of sorbitan, of ethoxylated sorbitan and of sorbitol, ethoxylated fatty acids, ethoxylated aliphatic alcohols, partial fatty acid esters of glycerol, ethoxy-lated partial fatty acid esters of glycerol, alkyldimethyl-benzyl-ammonium chloride, alkylammonium benzoate or lactate, cetylpyridinium chloride, dodecyl-di($\beta$-hydroxyethyl)benzylammonium chloride or soybean oil-trimethylammonium chloride, which can be used individually or as a mixture.

If appropriate, the liquid phase can also contain small amounts of other auxiliaries, such as, for example, colorants.

The pulverulent, solid component of the surgical material in particular consists, in a manner which is known per se, of the very fine-particled polymethyl methacrylate (average particle diameter up to 200 $\mu$m) and, if appropriate, small amounts of other modifying polyacrylate derivatives or copolymers thereof, such as, for example, methyl methacrylate/ethyl acrylate copolymers, methyl methacrylate/butyl methacrylate copolymers and methyl methacrylate/methyl acrylate or methyl methacrylate/butyl acrylate copolymers, the polymerization initiator—usually about 1-2% of dibenzoyl peroxide—and an X-ray contrast agent, such as, for example, zirconium dioxide, cerium dioxide, thorium dioxide, barium sulfate or calcium sulfate. This component can furthermore also contain other additives, such as antibiotics, biodegradable substances, such as tricalcium phosphate and collagen, bioactive glass ceramics or chopped reinforcing fibers of, for example, carbon, polyesters, polyvinyl alcohol or polyamide.

On application of the surgical material, for example frequently during implantation of an artificial hip joint, the sterile components, which are stored separately from one another, are stirred together in the particular amounts required to give a uniform paste and must then be processed comparatively rapidly, since the polymerization reaction starts very soon, with spontaneous heating, and the compositions harden completely after a short time.

The ratio of liquid to powder is about 0.4 to 0.75, the lower limit preferably being maintained in order to keep the monomer content low; on the other hand, the content of liquid should not be too low, because otherwise the viscosity of the mixed composition is too high and the composition is therefore less easy to stir.

The following examples have been carried out in order to demonstrate the properties of the surgical mixtures according to the invention. The properties were measured in accordance with the standard DIN-ISO 5833 for so-called bone cements. The residual monomer contents were determined by head space analysis by gas chromatography.

EXAMPLE 1

A liquid mixture consisting of 79% by weight of methyl methacrylate, 20% by weight of triacetin and 1% by weight of N,N-dimethyl-p-toluidine was prepared. The mixture is a clear homogeneous liquid at room temperature and runs out of an ampoule in a few seconds, without shaking being necessary.

18 g of this liquid mixture were mixed with 42 g of a powder mixture consisting of 88.6% by weight of polymethyl methacrylate powder, 10% by weight of zirconium dioxide powder and 1.4% by weight of dibenzoyl peroxide.

The following values of this surgical composition were measured in accordance with DIN-ISO 5833:
Hardening time at 24° C.: 11′ 30″
Maximum hardening temperature: 49.5° C.
Intrusion: 8 mm
Compressive strength: 87.5 MPa
Penetration depth: 0.166 mm
Resilience: 73.5%
Residual monomer content: 0.15%

EXAMPLES 2–9

The following liquid mixtures of 79% by weight of methyl methacrylate, 1% by weight of N,N-dimethyl-p-toluidine and in each case 20% by weight of
Example 2: glycerol diacetate
Example 3: glycol diacetate
Example 4: polyethylene glycol 400 (n=9)
Example 5: polyethylene glycol 420 (n=9.5)
Example 6: polypropylene glycol 620 (n=10.7)
Example 7: polypropylene glycol 1020 (n=17.6)
Example 8: diethyl L(+)-tartrate
Example 9: triethyl citrate were prepared.

In each case 18 g of these liquid mixtures, which were completely clear and homogeneous, were stirred with 42 g of the powder mixture described in Example 1, and the properties were measured in accordance with DIN-ISO 5833 and the residual monomer contents in the hardened bone cement were determined:

| Example | Maximum hardening temperature (°C.) | Intrusion (mm) | Compressive strength (MPa) | Penetration depth (mm) | Resilience (%) |
| --- | --- | --- | --- | --- | --- |
| 2 | 52.5° C. | 7.5 | 80.7 | 0.184 | 71.7 |
| 3 | 49° C. | 7 | 72.5 | 0.185 | 62.2 |
| 4 | 48° C. | 3.5 | 74.5 | 0.160 | 61.4 |
| 5 | 49° C. | 6.4 | 75 | 0.155 | 67.7 |
| 6 | 48° C. | 8.5 | 70.5 | 0.179 | 70.4 |
| 7 | 44.5° C. | 5.3 | 81.4 | 0.150 | 67.3 |
| 8 | 49.0° C. | x | 101.3 | 0.145 | 77.6 |
| 9 | 47° C. | x | 94.2 | 0.198 | 83 | xCould not be measured since the state of freedom from tackiness was not reached.

EXAMPLES 10–14

The following liquid mixtures were prepared with various types and amounts of organic liquids according to the invention:

| Example | MMA[1] | DMPT[2] | Liquid |
| --- | --- | --- | --- |
| 10 | 93% by weight | 2% by weight | 5% by weight of ethyl lactate |
| 11 | 88% by weight | 2% by weight | 10% by weight of ethyl lactate |
| 12 | 73% by weight | 2% by weight | 25% by weight of ethyl lactate |
| 13 | 78% by weight | 2% by weight | 20% by weight of triethyl citrate |
| 14 | 73% by weight | 2% by weight | 25% by weight of triethyl citrate |

[1]Methyl methacrylate
[2]N,N-Dimethyl-p-toluidine

In each case, 18 g of these mixtures, which were completely clear and homogeneous, were mixed with 42 g of the powder mixture described in Example 1, and the properties were measured in accordance with DIN-ISO 5833 and the residual monomer contents in the hardened composition were determined. The following results were found:

| Example | Maximum hardening temperature (°C.) | Compressive strength (MPa) | Penetration depth (mm) | Resilience (%) |
| --- | --- | --- | --- | --- |
| 10 | 51 | 114.2 | 0.153 | 75.2 |
| 11 | 47 | 107.1 | 0.149 | 75.2 |
| 12 | 39.5 | 70.3 | 0.207 | 60.2 |
| 13 | 41.5 | 100 | 0.161 | 72.0 |
| 14 | 39 | 80.5 | 0.198 | 66.6 |

All the compositions remained tacky during the processing time.

EXAMPLES 15 AND 16

The following liquid mixtures were prepared:

| | Example 15 | Example 16 |
| --- | --- | --- |
| Methyl methacrylate | 77% by weight | 76% by weight |
| N,N—Dimethyl-p-toluidine | 1.5% by weight | 1.5% by weight |
| Triethyl citrate | 20% by weight | 20% by weight |
| Polyoxyethylene(5)-sorbitan monooleate | 1.5% by weight | 2.5% by weight |

In each case 18 g of these clear and homogeneous mixtures were mixed with in each case 42 g of powder mixture according to Example 1, and the properties were measured in accordance with DIN-ISO 5833:

| Example | Maximum hardening temperature (°C.) | Compressive strength (MPa) | Penetration depth (mm) | Resilience (%) |
| --- | --- | --- | --- | --- |
| 15 | 45 | 96 | 0.172 | 78 |
| 16 | 42.5 | 92 | 0.185 | 75 |

After hardening, the residual monomer content of the various mixtures was determined by gas chromatography by the head space method, and the following values were measured:

| Example | Residual monomer content |
| --- | --- |
| 1 | 0.15% |
| 5 | 0.15% |
| 8 | 0.50% |
| 12 | 0.35% |
| 16 | 0.20% |

The novel surgical material with the addition, according to the invention, of the particular organic liquids has all the advantageous properties required of a high-quality bone cement, as has been shown by a comparison of its measurement data for compressive strength, which should be more than 70 MPa, its penetration depth, which should be not more than 0.2 mm, and its resilience, which should be more than 60%, with those of commercially available products. Moreover, in comparison with these products, it has a reduced maximum hardening temperature of 50° C. or less, and furthermore—as a result of the reduced monomer content—has a lower residual monomer content and significantly higher intrusion values, which is a measure of how capable the composition is of filling fine details in the still plastic state, and is thus equally as good as a bone cement according to German Pat. No. 2,552,070, without having the disadvantages described for an emulsion.

We claim:

1. A bone cement based on liquid monomeric and pulverulent polymeric acrylates and/or methacrylates, catalysts and accelerators which bone cement passes via a plastic state into a solid state by mixing of the liquid and pulverulent components, which bone cement contains a liquid component consisting essentially of 1–15% by weight, based on the total weight of the bone cement, of a further liquid substance consisting essentially of one or more non-toxic, aliphatic esters selected from the group consisting of glycol mono-formate, -acetate, -propionate, -glycolate and -lactate;
glycol di-formate, -acetate, -propionate, -glycolate and -lactate;
glycerol mono-formate, -acetate, -propionate, -glycolate and -lactate;
glycerol di-formate, -propionate, -glycolate and -lactate;
glycerol tri-formate, -priopionate, -glycolate and -lactate;
methyl-, ethyl-, propyl- and butyl-glycolate;
methyl-, ethyl-, propyl- and butyl-lactate;
monomethyl- and dimethyl-malate;
monoethyl- and diethyl-malate;
monopropyl- and dipropyl-malate;
monobutyl- and dibutyl-malate;
monomethyl- and dimethyl-tartrate;
monoethyl- and diethyl-tartrate;
monopropyl- and dipropyl-tartrate;
monobutyl-tartrate;
mono-, di- and trimethyl-citrate;
mono-, di- and triethyl-citrate;
mono-, di- and tripropyl-citrate;
mono-, di- and tributyl-citrate;
these liquid esters having a boiling point above 100° C.

2. A bone cement as claimed in claim 1, wherein the liquid esters have a ratio of non-polar to polar groups of 1:1 to 3:1, non-polar groups being —CH$_3$, —CH$_2$—,

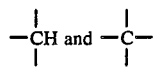

and polar groups being —OH, —O— and —COOR.

3. A bone cement as claimed in claim 1, wherein the liquid ester is, triethyl citrate.

4. A bone cement as claimed in claim 1, which contains 5–30% by weight, of the liquid ester in the liquid component.

5. A bone cement as claimed in claim 1, wherein the liquid component contains up to 5% of a surface-active substance.

6. A bone cement as claimed in claim 1, wherein the ratio of powder to liquid component is 1:1 to 3:1.

7. A bone cement as claimed in claim 1, wherein said boiling point is above 150° C.

8. A bone cement as claimed in claim 1, which further includes an additive selected from the group consisting of antibiotics, collagen, bioactive glass ceramics and chopped reinforcing fibers.

9. A bone cement as claimed in claim 1, which contains 15–20% by weight of the liquid ester in the liquid component.

10. A bone cement as claimed in to claim 1, wherein the ratio of powder to liquid component is 1.5:1 to 2.5:1.

11. A surgical material as claimed in claim 1, wherein the liquid component contains 94.5–62% by weight of monomeric methyl methacrylate, 5–30% by weight liquid esters, 0.5–3% by weight of an accelerator and 0–5% by weight of surface active substances.

12. A bone cement as claimed in claim 1, wherein the methacrylate is methyl methacrylate which is stabilized with 50–100 ppm of hydroquinone or hydroquinone monomethyl ester.

13. A bone cement as claimed in claim 1, wherein the accelerator is selected from the group consisting of N,N-Dimethyl-p-toluidine, N,N-dimethylaniline, N,N-dimethylxylidines, N,N-dimethyl-anisidines and N-monomethylanisidines.

14. A bone cement as claimed in claim 5, wherein the surface active substance is selected from the group consisting of fatty acid esters of sorbitan, fatty acid esters of sorbitol, ethoxylated fatty acids, ethoxylated aliphatic alcohols, ethoxylated partial fatty acid esters of glycerol, alkydimethyl-benzyl-ammonium chloride, alkylammonium benzoate, alkylammonium lactate, cetylpyridinium chloride, dodecyl-di(beta-hydroxyethyl)-benzyl-ammonium chloride, soybean oil-trimethylammonium chloride and mixtures thereof.

15. A bone cement as claimed in claim 1, wherein said pulverulent polymeric acrylates and/or methacrylates contain modifying polyacrylate derivatives or copolymers thereof selected from the group consisting of methyl methacrylate/ethyl acrylate copolymers, methyl methacrylate/butyl methacrylate copolymers, methyl methacrylate/methyl acrylate and methyl methacrylate/butyl acrylate copolymers.

* * * * *